United States Patent [19]

Lantzsch

[11] Patent Number: 5,623,076

[45] Date of Patent: Apr. 22, 1997

[54] PROCESS FOR THE PREPARATION OF CHLOROMETHYLPYRIDINES

[75] Inventor: Reinhard Lantzsch, Wuppertal, Germany

[73] Assignee: Bayer Aktiengesellschaft, Leverkusen, Germany

[21] Appl. No.: 573,714

[22] Filed: Dec. 18, 1995

[30] Foreign Application Priority Data

Dec. 23, 1994 [DE] Germany ............................ 44 46 338.3

[51] Int. Cl.$^6$ ...................... C07D 213/26; C07D 213/61; C07D 213/38
[52] U.S. Cl. ........................... 546/345; 546/325; 546/337
[58] Field of Search ...................................... 546/345, 337, 546/325

[56] References Cited

U.S. PATENT DOCUMENTS

| | | | |
|---|---|---|---|
| 4,778,896 | 10/1988 | Gallenkamp | 546/304 |
| 4,990,622 | 2/1991 | Jelich | 546/345 |
| 5,116,993 | 5/1992 | Jelich | 546/345 |
| 5,198,549 | 3/1993 | Günther | 546/345 |

FOREIGN PATENT DOCUMENTS

| | | |
|---|---|---|
| 0556684 | 8/1993 | European Pat. Off. . |
| 0691331 | 1/1996 | European Pat. Off. . |
| 9518122 | 7/1995 | WIPO . |

OTHER PUBLICATIONS

Chemical Abstracts, vol. 116, abstract No. 59366r, p. 862, abstract of JP 03–223,252, (1992).

J.W. Tilley, et al., J. Heterocyclic Chem., vol. 16, pp. 333–337, (1979).

J.v. Braun, et al., Justus Liebigs Annalin der Chemie, vol. 449, No. 2/3, pp. 249–277, (1926).

W.R. Vaughan, et al., J. Am. Chem. Soc., vol. 84, No. 5, pp. 769–774, (1962).

J.F. Bieron, et al., in "The Chemistry of Amides", J. Zabicky ed., Ch. 4, pp. 245–288, Interscience Publishers (New York). 1970.

R. Tachikawa, et al., Heterocycles, vol. 15, No. 1, pp. 369–371, (1981).

O. Meth–Cohn, et al., J. Chem. Soc., Perkin I, pp. 1537–1543, (1981).

*Primary Examiner*—C. Warren Ivy
*Assistant Examiner*—D. Margaret M. Mach
*Attorney, Agent, or Firm*—Sprung Horn Kramer & Woods

[57] ABSTRACT

The invention relates to a new process for the preparation of chloromethylpyridines of the general formula (I)

$$\underset{Cl}{\underset{|}{X^1}}\text{-pyridine-}CH_2Cl \quad (I)$$

in which $X^1$ represents hydrogen, halogen or alkyl, characterized in that pyridine derivatives of the general formula (II)

$$\underset{Cl}{\underset{|}{X^1}}\text{-pyridine-}CH_2-NH-CO-R^1 \quad (II)$$

in which $R^1$ and $X^1$ have the meaning given in the description, are reacted by means of a formamide derivative of the general formula (III)

$$\begin{array}{c} R^2 \\ \diagdown \\ N-CHO \\ \diagup \\ R^3 \end{array} \quad (III)$$

in which $R^2$ and $R^3$ are identical or different and represent alkyl or cycloalkyl or together represent alkanediyl, and with a chlorinating agent, if appropriate in the presence of a diluent, at temperatures between 20° and 120° C. The invention furthermore relates to new pyridine derivatives of the formula (II) and their preparation.

3 Claims, No Drawings

PROCESS FOR THE PREPARATION OF CHLOROMETHYLPYRIDINES

The invention relates to a new process for the preparation of chloromethylpyridines and to new intermediates for their preparation.

It is known that chloromethylpyridines can be obtained by reaction of hydroxymethylpyridines with thionyl chloride (cf. J. Heterocycl. Chem. 16 (1979), 333–337; cf. also EP-A 373 464).

It is furthermore known that chloromethylpyridines are obtained when methylpyridines are chlorinated in the presence of acid acceptors or agents which form free radicals and in the presence of inert diluents at temperatures between 0° C. and 100° C. (cf. EP-A 260 485, cf. also EP A 458 109).

It is furthermore known that alkoxymethylpyridines can also be converted into chloromethylpyridines by reaction with suitable chlorinating agents (cf. EP-A 393 453).

It is also known that chloromethylpyridines can be obtained from corresponding aminomethylpyridines by diazotization in the presence of, for example, hydrogen chloride (cf. JP 05 178 835).

However, with these known synthesis methods, the yields which can be achieved and the qualities of the products are not always satisfactory.

It has now been found that chloromethylpyridines of the general formula (I)

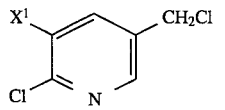

in which

X$^1$ represents hydrogen, halogen or alkyl, are obtained in good yields and in a high purity if pyridine derivatives of the general formula (II)

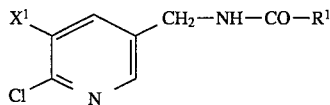

in which

R$^1$ represents hydrogen, alkyl or optionally substituted phenyl and

X$^1$ has the abovementioned meaning are reacted by means of a "Vilsmeier reagent", i.e. with a formamide derivative of the general formula (III)

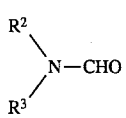

in which

R$^2$ and R$^3$ are identical or different and represent alkyl or cycloalkyl or together represent alkanediyl, and with a chlorinating agent, if appropriate in the presence of a diluent, at temperatures between 20° and 120° C. and the product is then worked up in the customary manner.

Surprisingly, chloromethylpyridines of the formula (I) can be obtained in very good yields and in a high purity by the process according to the invention, although according to the prior art on the one hand formylation of the NH group was to be expected (cf., for example, J. C. S. Perkin I, pages 1537–1543 (1981)); and on the other hand the reaction does not take place according to the "von Braun reaction" (cf., JACS 84, 769–774 (1962)) with phosphorus pentachloride or sulphonyl chloride as the chlorinating agent.

The invention preferably relates to chloromethylpyridines of the formula (I), in which X$^1$ represents hydrogen, chlorine or methyl, which are to be prepared by the process according to the invention.

If, for example, 2,3-dichloro-5-acetaminomethylpyridine is used as the starting substance and dimethylformamide and oxalyl chloride are used as the "Vilsmeier reagent", the come of the reaction in the process according to the invention can be outlined by the following equation:

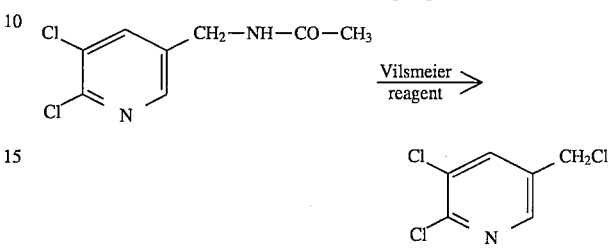

Formula (II) provides a general definition of the pyridine derivatives to be used as starting substances in the process according to the invention. In formula (II), X$^1$ preferably has that meaning which has already been mentioned above as preferred for X$^1$ in connection with the description of the compounds of the formula (I) to be prepared according to the invention. R$^1$ preferably represents hydrogen, or represents straight-chain or branched alkyl having 1 to 4 carbon atoms, such as, in particular, methyl and ethyl, or represents phenyl which is optionally mono- to trisubstituted by identical or different substituents, substituents which may be mentioned being: halogen, such as, in particular, fluorine or chlorine; straight-chain or branched alkyl having 1 to 4 carbon atoms, such as, in particular, methyl, ethyl or isopropyl; straight-chain or branched alkoxy and alkylthio having in each case 1 to 2 carbon atoms, such as, in particular, methoxy or methylthio; straight-chain or branched halogenoalkyl, halogenoalkoxy and halogenoalkylthio having in each case 1 to 2 carbon atoms and 1 to 5 identical or different halogen atoms, such as fluorine and chlorine atoms, such as, in particular, trifluoromethyl, trifluoromethoxy or trifluoromethylthio; and phenyl which is optionally substituted by chlorine and/or methyl.

The pyridine derivatives of the formula (II) are known in some cases (cf. EP-A 0 556 684). Pyridine derivatives which are not yet known and to which the present invention likewise relates are those of the general formula (IIa)

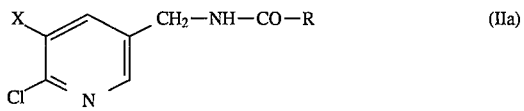

in which

X represents hydrogen, halogen or alkyl and

R represents alkyl or optionally substituted phenyl.

Preferred pyridine derivatives of the formula (IIa) are those in which

X represents hydrogen, chlorine or methyl,

R represents straight-chain or branched alkyl having 1 to 4 carbon atoms, such as, in particular, methyl and ethyl; or represents phenyl which is optionally mono- to trisubstituted by identical or different substituents, substituents which may be mentioned being: halogen, such as, in particular, fluorine or chlorine; straight-chain or branched alkyl having 1 to 4 carbon atoms, such as, in particular, methyl and ethyl, or represents phenyl which is optionally mono- to trisubstituted by identical or different substituents, substituents which may be mentioned being: halogen, such as, in particular, fluorine or chlorine, straight-chain or branched alkyl having 1 to 4 carbon atoms, such as, in particular, methyl, ethyl or isopropyl; straight-chain or branched alkoxy and alkylthio having in each cage 1 to 2 carbon atoms, such as, in particular, methoxy or methylthio; straight-chain or branched halogenoalkyl, halogenoalkoxy and halogenoalkylthio having in each case 1 to 2 carbon atoms and 1 to 5 identical or different halogen atoms, such as fluorine and chlorine atoms, such as, in particular, trifluoromethyl, trifluoromethoxy or trifluoromethylthio; and phenyl which is optionally substituted by chlorine and/or methyl.

The new pyridine derivatives of the formula (IIa) are obtained by a process in which aminomethylpyridines of the general formula (IV)

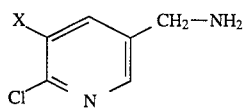 (IV)

in which

X has the abovementioned meaning,
are reacted with acid chlorides of the general formula (V)

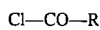 (V)

in which

R has the abovementioned meaning,
in the presence of a reaction auxiliary and if appropriate in the presence of a diluent.

Possible diluents for carrying out the process for the preparation of the pyridine derivatives of the formula (IIa) are all the inert organic solvents which are customary for such reactions. Solvents which can preferably be used are esters, such as methyl acetate or ethyl acetate, and furthermore ethers, such as diethyl ether, methyl tert-butyl ether, ethylene glycol dimethyl ether, tetrahydrofuran and dioxane, and furthermore nitriles, such as acetonitrile, and in addition optionally halogenated aliphatic, cycloaliphatic and aromatic hydrocarbons, such as methylenechloride, chloroform, carbon tetrachloride, hexane, cyclohexane, benzene, toluene, xylene and chlorobenzene.

Possible reaction auxiliaries in carrying out the process for the preparation of the pyridine derivatives of the formula (IIa) are all the customary inorganic or organic bases. Bases which can preferably be used are alkalimetal or alkaline earth metal hydroxides, amides, alcoholates, carbonates and bicarbonates, such as sodium hydroxide, potassium hydroxide, sodium amide, sodium methylate, sodium ethylate, potassium tert-butylate, sodium carbonate, potassium carbonate, calcium carbonate, potassium bicarbonate and sodium bicarbonate, and furthermore tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

The reaction temperatures can be varied within a substantial range in carrying out the process for the preparation of the pyridine derivatives of the formula (IIa). The reaction is in general carried out at temperatures between 0° and 120° C., preferably between 10° and 100° C.

In carrying out the process for the preparation of the pyridine derivatives of the formula (IIa), in general 1.0 to 3.0 mol, preferably 1.0 to 1.5 mol, of acid chloride of the formula (V) and 1.0 to 3.0 mol, preferably 1.0 to 1.5 mol, of reaction auxiliary are employed per mole of aminomethylpyridine of the formula (IV). The reaction is carried out and the reaction products are worked up and isolated by generally customary methods.

The aminomethylpyridines of the formula (IV) are known (cf., for example, U.S. Pat. No. 5,300,650, EP-A 0 579 970), or they can be obtained in a known manner by the processes described therein.

The acid chlorides of the formula (IV) are generally known compounds of organic chemistry.

The new pyridine derivatives of the formula (IIa) can also be obtained by reacting aminomethylpyridines of the formula (IV) with corresponding anhydrides in a generally known manner.

Formula (III) provides a general definition of the formamide derivatives furthermore to be used as starting substances in the process according to the invention. In the formula (III) $R^2$ and $R^3$ are identical or different and preferably represent straight-chain or branched alkyl having 1 to 6 carbon atoms, such as, in particular, methyl, ethyl, n- or i-propyl or n-, i-, s- or t-butyl; or furthermore represent cycloalkyl having 3 to 6 carbon atoms, such as, in particular, cyclopentyl or cyclohexyl; or together represent alkanediyl having 2 to 6 carbon atoms, such as, in particular, butane-1,4-diyl or pentane-1,5-diyl.

Examples which may be mentioned of the formamide derivatives of the formula (III) are: N,N-dimethyl-formamide, N,N-diethyl-formamide, N,N-dipropyl-formamide, N,N-dibutyl-formamide, N-cyclohexyl-N-methyl-formamide and N,N-dicyclohexylformamide.

N,N-dimethyl-formamide and N,N-dibutyl-formamide may be mentioned as particularly preferred formamide derivatives.

The formamide derivatives of the formula (III) are known organic synthesis chemicals.

The process according to the invention is carried out using a chlorinating agent. The customary chlorinating agents can be used here, for example phosphoryl chloride (phosphorus oxychloride), phosphorus(V) chloride, phosgene, oxalyl chloride, thionyl chloride, perchlorobutanoic acid chloride, dichlorobenzodioxole, N,N-dimethylchloromethylimmonium chloride or N,N-diethyl-chloromethylimmonium chloride.

Phosgene is particularly preferred as the chlorinating agent in the process according to the invention.

Possible diluents for carrying out the process according to the invention are the customary organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, methylene chloride, chloroform and carbon tetrachloride; ethers, such as diethyl ether, diisopropyl ether, dioxane, tetrahydrofuran or ethylene glycol dimethyl or diethyl ether; nitriles, such as acetonitrile, propionitrile or butyronitrile; amides, such as N,N-dimethylformamide, N,N-dimethylacetamide, N-methylformanilide, N-methylpyrrolidone or hexamethylphosphoric acid triamide; sulphoxides, such as dimethyl sulphoxide, and sulphones, such as tetramethylene sulphone.

Chlorobenzene, acetonitrile and butyronitrile may be mentioned as particularly preferred diluents.

The reaction temperatures can be varied within a substantial range in carrying out the process according to the invention. The reaction is in general carried out at temperatures between −30° C. and +150° C., preferably at temperatures of between −10° C. and +120° C., the reaction preferably being carried out at between −10° C. and +40° C. in the initial phase and then between +20° C. and 120° C. However, the reaction can also be carried out directly at elevated temperature and the "Vilsmeier reagent" can be generated in situ.

The process according to the invention is in general carried out under normal pressure. However, it is also possible for the process to be carried out under increased or reduced pressure—in general between 0.1 bar and 10 bar.

For carrying out the process according to the invention, in general between 1 and 10 mol, preferably between 1.5 and 5.0 mol, in particular between 2.0 and 4.0 mol, of chlorinating agent and between 1 and 10 mol, preferably between 2.0 and 4.0 mol, of formamide derivative of the formula (III) are employed per mole of pyridine derivative of formula (II).

The reaction components can be reacted with one another in any desired sequence in carrying out the process according to the invention.

In a preferred embodiment of the process according to the invention, the formamide derivative of the formula (III) and the chlorinating agent are first initially introduced into a diluent and the pyridine derivative of the formula (II) is then metered in at temperatures between −10° C. and +50° C. The reaction is then brought to completion by stirring at elevated temperature for one or more hours.

Working up can be carried out in the customary manner. For example, the mixture is diluted to two to three times the volume with water. The aqueous phase is brought to a pH of between 2 and 7 by addition of a base, such as, for example, sodium hydroxide solution, and is then extracted by means of a solvent, and this solvent is then distilled off thoroughly under reduced pressure. The crude product which remains as the residue can be further purified in the customary manner; however, it can also be used as such for further reactions. Isolation by steam distillation is also possible.

The chloromethylpyridines of the formula (I) to be prepared by the process according to the invention can be used as intermediates for the preparation of biologically active compounds, for example insecticides (cf. EP-A 163 855 and EP-A 192 060).

PREPARATION EXAMPLES

Example 1

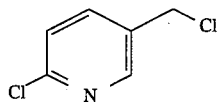

4.95 g (0.02 mol) of 2-chloro-5-benzoylaminopyridine (cf. Example IIa-2) and 4.4 g (0.06 mol) of dimethylformamide are dissolved in 20 ml of butyronitrile. 6.6 g of phosgene are then passed in, without cooling. The mixture is then heated at 50° C. for 5 hours and at 115° C. for one hour.

After cooling, the mixture is poured onto ice-water and extracted three times with methylene chloride. The combined organic phases are dried and concentrated. The black oil which remains is purified by distillation in a bulb tube (oil pump vacuum; jacket temperature 70°–80° C.).

1.8 g (55.6% of theory) of 2-chloro-5-chloromethylpyridine of melting point 35°–36° C. are obtained.

Example 2

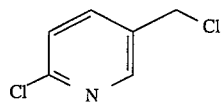

37 g (0.2 mol) of 2-chloro-5-acetaminomethylpyridine (cf. Example IIa-1) and 44 g (0.06 mol) of dimethylformamide are dissolved in 200 ml of acetonitrile. 76 g (0.06 mol) of oxalyl chloride are added dropwise at 15° C. and the mixture is then heated to 80° C. It is stirred at this temperature for 18 hours, cooled and poured onto ice-water. After the mixture has been extracted three times with methylene chloride, the organic phases are dried and concentrated. 24 g of a black oil are obtained and are purified by distillation. 23.4 g (72.2% of theory) of 2-chloro-5-chloromethylpyridine of melting point 35°–36° C. are obtained.

Example 3

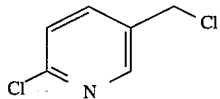

The reaction is carried out analogously to Example 2, but instead of 76 g of oxalyl chloride, 60 g of phosgene are employed.

24.2 g (74.7% of theory) of 2-chloro-5-chloromethylpyridine of melting point 35°–36° C. are obtained.

PREPARATION OF THE PRECURSORS OF THE FORMULA (IIa)

Example (IIa-1)

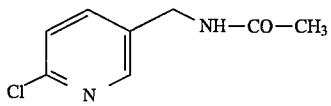

28.5 g (0.2 mol) of 2-chloro-5-aminomethylpyridine and 22.2 g (0.22 mol) of triethylamine are dissolved in 300 ml of ethyl acetate. 16.5 g (0.21 mol) of acetyl chloride are then added dropwise at 20° C., while cooling. The mixture is subsequently stirred overnight, washed twice with water, dried and concentrated.

30.5 g (83% of theory) of 2-chloro-5-acetaminomethylpyridine are obtained as pale yellow crystals of melting point 76°–77° C.

Example (IIa-2)

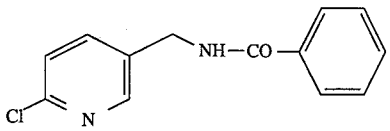

14.25 g (0.1 mol) of 2-chloro-5-aminomethylpyridine and 11.1 g (0.11 mol) of triethylamine are dissolved in 150 ml of methylene chloride. 14.8 g (0.105 mol) of benzoyl chloride are then added dropwise at about 20° C. and the reaction mixture is subsequently stirred overnight at room temperature. It is washed three times with water and the organic phase is dried and concentrated. 24.6 g (99.8% of theory) of 2-chloro-5-benzoylaminopyridine are obtained as white crystals of melting point 118°–120° C.

I claim:

1. Process for the preparation of chloromethylpyridines of the general formula (I)

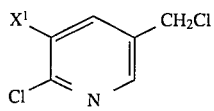   (I)

in which $X^1$ represents hydrogen, halogen or alkyl, characterized in that pyridine derivatives of the general formula (II)

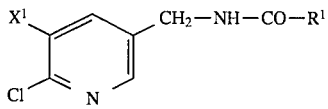   (II)

in which $R^1$ represents hydrogen, alkyl or optionally substituted phenyl and $X^1$ has the abovementioned meaning are reacted by means of a formamide derivative of the general formula (III)

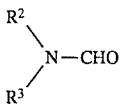   (III)

in which $R^2$ and $R^3$ are identical or different and represent alkyl or cycloalkyl or together represent alkanediyl, and with a chlorinating agent, if appropriate in the presence of a diluent at temperatures between 20° and 120° C.

2. Pyridine derivatives of the general formula (IIa)

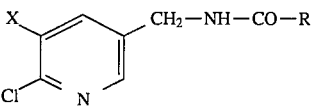   (IIa)

in which

X represents hydrogen, halogen or alkyl and

R represents alkyl or optionally substituted phenyl.

3. Process for the preparation of the pyridine derivatives of the formula (IIa), characterized in that aminomethylpyridines of the general formula (IV)

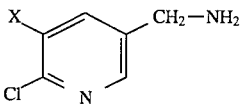   (IV)

in which

X represents hydrogen, halogen or alkyl, are reacted with acid chlorides of the general formula (V)

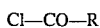   (V)

in which

R represents alkyl or optionally substituted phenyl, in the presence of a reaction auxiliary and if appropriate in the presence of a diluent.

\* \* \* \* \*